(12) United States Patent
Yoshizumi

(10) Patent No.: US 6,572,525 B1
(45) Date of Patent: Jun. 3, 2003

(54) NEEDLE HAVING AN APERTURE FOR DETECTING SEEDS OR SPACERS LOADED THEREIN AND COLORED SEEDS OR SPACERS

(76) Inventor: Lisa Yoshizumi, 7115-46th Ave. South, Seattle, WA (US) 98118

( * ) Notice: Subject to any disclaimer, the term of this patent is extended or adjusted under 35 U.S.C. 154(b) by 0 days.

(21) Appl. No.: 09/579,429

(22) Filed: May 26, 2000

(51) Int. Cl.⁷ .......................... A61M 36/00; A61N 5/00
(52) U.S. Cl. ......................................................... 600/7
(58) Field of Search ................................ 600/1, 2, 3, 4, 600/5, 6, 7, 8, 427

(56) References Cited

U.S. PATENT DOCUMENTS

| | | | |
|---|---|---|---|
| 4,086,914 A | 5/1978 | Moore | 128/1.2 |
| 4,763,642 A | 8/1988 | Horowitz | 128/1.2 |
| 4,763,671 A | 8/1988 | Goffinet | 128/786 |
| 4,815,449 A | 3/1989 | Horowitz | 600/7 |
| 5,242,373 A | 9/1993 | Scott et al. | 600/7 |
| 5,860,909 A | 1/1999 | Mick et al. | 600/7 |
| 5,924,973 A * | 7/1999 | Weinberger | 600/3 |
| 5,928,130 A | 7/1999 | Schmidt | 600/7 |
| 5,938,583 A | 8/1999 | Grimm | 600/7 |
| 6,010,446 A | 1/2000 | Grimm | 600/3 |
| 6,030,333 A | 2/2000 | Sioshansi et al. | 600/3 |
| 6,129,670 A * | 10/2000 | Burdette et al. | 600/427 |
| 6,221,003 B1 * | 4/2001 | Sierocuk et al. | 600/7 |
| 6,402,677 B1 * | 6/2002 | Jacobs | 600/7 |

* cited by examiner

Primary Examiner—Max F. Hindenburg
Assistant Examiner—Brian Szmal
(74) Attorney, Agent, or Firm—Dorsey & Whitney LLP

(57) ABSTRACT

The invention provides a device for use in brachytherapy applications for implanting seeds and spacers into tissue that includes a needle or shaft having an aperture or slit down the side that exposes the interior space of the shaft to allow the sequence of seeds and spacers to be detected by observing their position through the aperture. The invention also provides colored seeds and/or colored spacers that facilitate visual detection of a load sequence of seeds and spacers in any brachytherapy device. Methods and systems using the needle or shaft having a slit, or for using the colored seeds or spacers, are also provided.

57 Claims, 7 Drawing Sheets

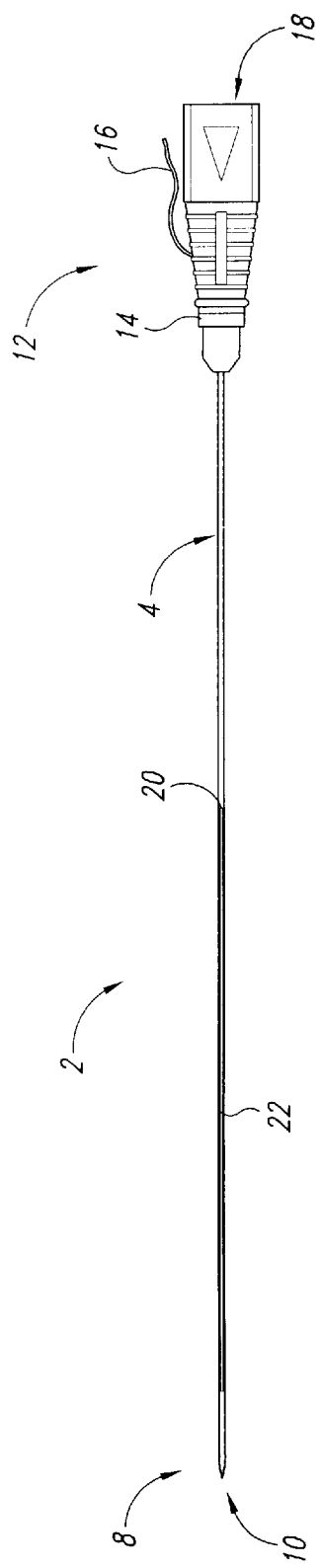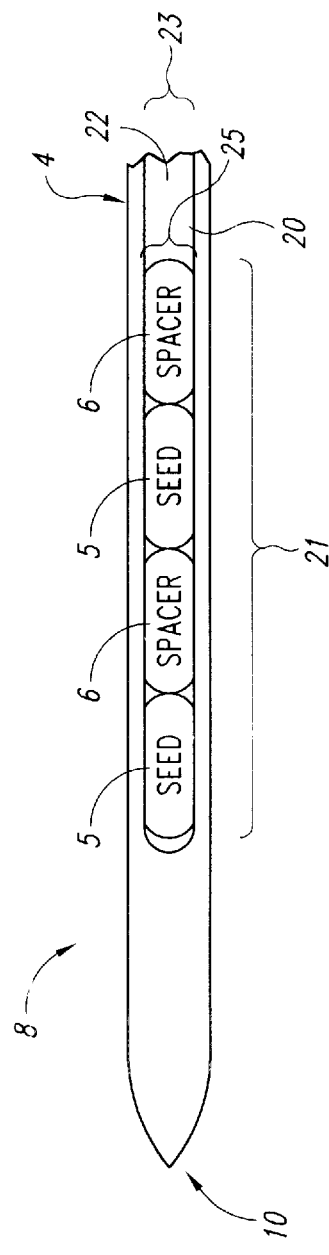
Fig. 1A
Fig. 1B

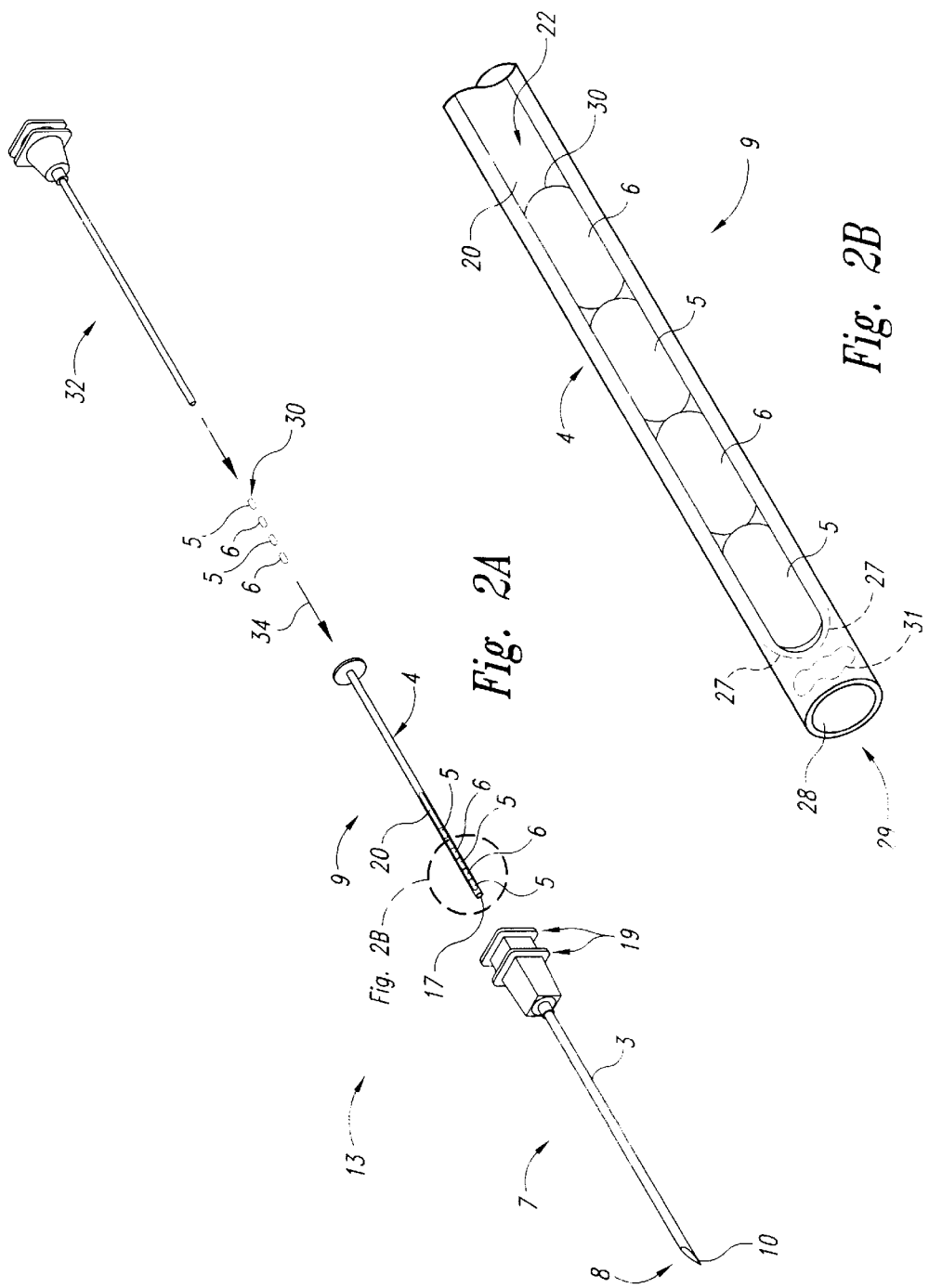

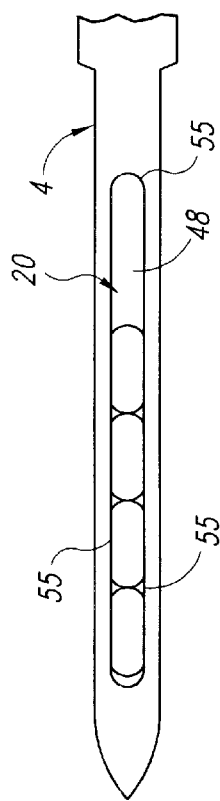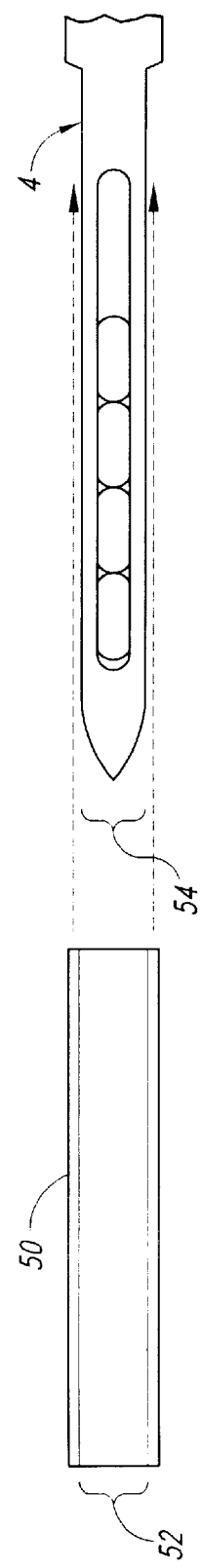
Fig. 4A
Fig. 4B

NEEDLE HAVING AN APERTURE FOR DETECTING SEEDS OR SPACERS LOADED THEREIN AND COLORED SEEDS OR SPACERS

TECHNICAL FIELD

The invention relates to brachytherapy devices for implanting radioactive seeds into a patient's body for treatment of cancer. More specifically, the invention relates to a needle with an aperture on the shaft that permits visual inspection of a sequence of radioactive seeds and spacers loaded into the needle. In addition, the invention relates to seeds or spacers that are colored to facilitate visual detection of the same when loaded into a brachytherapy device.

Brachytherapy is a cancer treatment regiment that includes interstitial implanting of radioactive seeds directly into tumors in a patient's body. Brachytherapy is particularly suitable for localized tumors that can be directly reached using needles and catheters. Treatment of prostate cancer is an example of condition where brachytherapy is a preferred procedure. According to the American Cancer Society, upwards of 180,000 men in the United States will be diagnosed with prostate cancer each year. Prostate treatment options typically have included radical prostatectomy (removal of the prostate) and external beam radiation. Both these methods result in unwanted destruction of non-tumorgenic tissue with corresponding adverse side-effects. The newer brachytherapy method involves permanently implanting tiny radioactive "seeds" directly into the prostate to kill cancer cells. This is becoming the treatment of choice because the radiation is concentrated in the affected area and avoids many of the side-effects associated with other treatment methods, including incontinence, impotence and hormonal imbalance. Current estimates show that over 25% of prostate cancer patients will choose prostate brachytherapy (radioactive seed implants) or other seed implant procedures, and this number is expected to rise as techniques and equipment used for the procedure improve.

The success of a seed implant therapy depends greatly on the precise placement of the seeds within the tissue containing the tumor. This is particularly true in tumors located in tissues with closely associated structures that could be damaged by improper implantation. For example, in the case of prostate cancer, the physician must be able to insert the seeds without interfering with the urethra (which goes through the prostate) or the rectum (which is below the prostate) while ensuring that the proper radiation dosage is being delivered to the entire prostate. To facilitate proper localization of the tumor and proper procedure for implanting seeds, a dosimetrist will use a computer system to prepare treatment "maps" by using images taken from a transrectal ultrasound study to determine the best placement for the seeds so as to deliver an optimal dose of radiation. For a typical treatment plan in prostate cancer, an average of 120 seeds will be prescribed and 20–25 needles will be used in a three-dimensional array to implant the seeds at proper locations determined according to the treatment maps. The treatment plan typically includes instructions for what needles are to be inserted into which position in the tumor, and how many seeds are to be loaded into each needle according to a precise spacing pattern that corresponds to the implant locations determined by the map. The spacing pattern in the needle is set by alternatively loading a radioactive seed or a non-radioactive spacer in a particular load sequence. For optimal therapeutic benefit without adverse side-effects, it is essential that the needles have the correct load sequence of seeds and spacers determined according to the treatment plan.

However, the current needles and brachytherapy devices used for implanting seeds and spacers do not allow the person using the device to detect and confirm the load sequence of seeds and spacers after they have been loaded into the device. Improper loading can lead to a deviation from the treatment plan and cause areas to be treated with too much radiation or too little radiation in particular spots. This is especially true when the area around the urethra or other parts is implanted, because improper implanting may cause loose seeds to migrate into the urethra increasing the probability that seeds may be expelled and/or result in acute/long-term side-effects.

Current device loading practice dictates that if a technician is manually loading seeds or spacers into the device and cannot confirm correct placement of a seed or a spacer, the technician must empty the device and begin again. This safety practice can result in substantially increased cost in providing brachytherapy applications. Operating room costs in the U.S. typically are in the range of $25–75 per minute. Unloading and reloading a device can take several minutes to complete. Therefore, a mistake, if discovered, can quickly add large and unnecessary expense to a brachytherapy procedure. If undiscovered, it can result in hot spots or cold spots as a result of too much or not enough radiation being provided.

Accordingly, there is a need in the art to lessen the problems associated with an improperly loaded brachytherapy device by facilitating detection of the load sequence of seeds and spacers used therein. The present invention is directed to this need.

SUMMARY

In one aspect, there is provided, a device for implanting radioactive seeds and spacers into tissue that includes, a shaft enclosing an interior space for receiving a load sequence of seeds and spacers. The shaft contains an aperture positioned along a portion of the shaft that exposes a sufficient portion of the interior space to allow the load sequence of seeds and spacers to be detected after the load has been received into the shaft. In one embodiment, the aperture is a slit down the longitudinal axis of the shaft, the seeds are radioactive seeds used in brachytherapy applications, and the brachytherapy is used for treatment of prostate cancer. The shaft may be a needle for direct insertion of the load of seeds and spacers, or can be a sleeve member subsequently received into another member such as a needle or catheter for implanting the load of radioactive seeds and spacers.

In another aspect, there is provided, colored seeds or spacers that facilitate direct visual detection of the load sequence of seeds and spacers in any brachytherapy application. In this regard, the invention provides a seed for implanting into tissue in a load sequence with a spacer, wherein the seed is colored with a biologically acceptable dye to identify the seed. It also provides a spacer for implanting into tissue in a load sequence with a radioactive seed, wherein the spacer is colored with a biologically acceptable dye to identify the spacer. More specifically, this aspect provides a system for detecting a load sequence of seeds and spacers in a loading shaft, wherein at least one of the seeds or spacers is colored with a biologically acceptable dye to provide an identifying color that distinguishes the seeds from the spacers. In certain embodiments, the seeds,, the spacers or both are colored. The coloration of the seeds or spacers may be according to criteria such as isotope type, material type, dose, assay date or manufacturer to help facilitate confirmation of the proper load sequence.

In related aspects, there are provided, methods for detecting a load sequence of seeds and spacers in a brachytherapy device that includes use of the aforementioned devices and systems, and/or the colored seeds and/or spacers. These include methods using both the aperture containing shaft and the colored spacers or seeds to facilitate confirmation of the load sequence of radioactive seeds and spacers in brachytherapy applications. The benefits of these and other aspects of these methods, systems and devices will be apparent to one of ordinary skill in the art in light of the following description and accompanying figures.

DESCRIPTION OF THE DRAWINGS

FIG. 2 illustrates another embodiment that includes a multi component needle assembly having an insertion shaft that contains an aperture for detecting a load sequence of seeds and spacers.

FIG. 4 illustrates embodiments where the aperture is covered by a transparent or translucent material.

DETAILED DESCRIPTION CERTAIN EMBODIMENTS

Figure 1C:
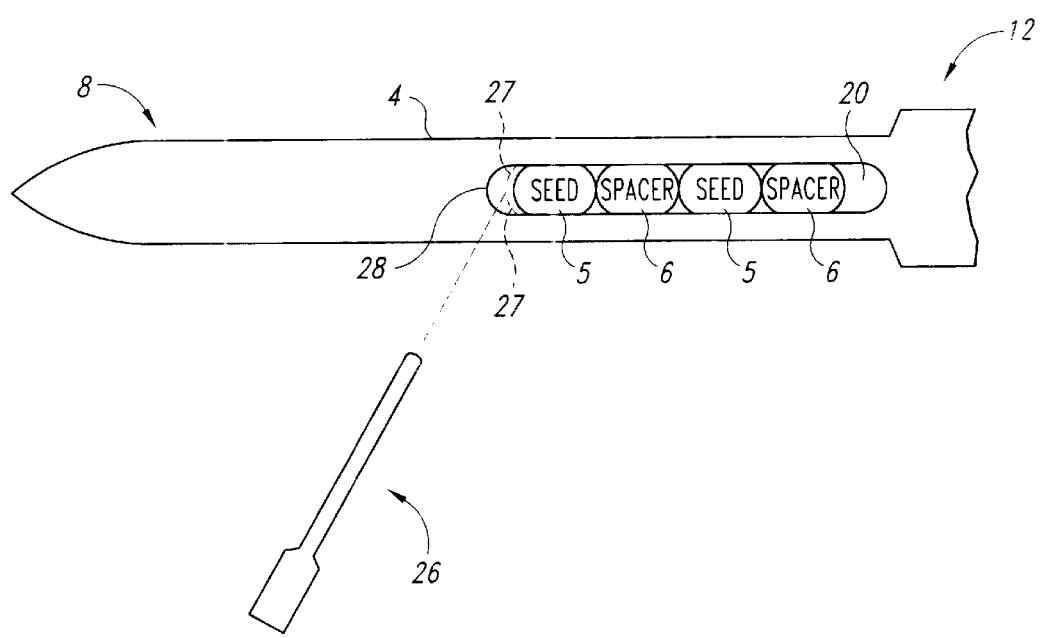
FIG. 1 illustrates one embodiment which is a needle having a longitudinal aperture positioned along a portion of a shaft for detecting a load sequence of seeds and spacers.

Prior to setting forth the present invention in detail, the following terms are herein defined to aid in an understanding thereof.

A "seed" is a therapeutic or diagnostic material inserted into the tissue of an animal for treatment of a disease. Typically, a seed is small solid material comprised of a radioactive isotope that is implanted into tumor tissue. While the description of several embodiments is illustrated with reference radioactive seeds used in brachytherapy applications, other embodiments, include seeds where the therapeutic or diagnostic material may include, for example, a drug or biological agent such as a virus, or a diagnostic reagent, such as an immunological reagent that reacts with certain tissue but not others, where in any case the seed is delivered locally to tissue by way of a seed implanting step.

A "spacer" is a material inserted with a seed that is not intended to have a therapeutic or diagnostic effect, but rather is intended to aid in the spatial distribution of seeds inserted into tissue. Spacers are available in a variety of shapes and sizes and are typically made of a biologically acceptable material such as suture material (cat gut).

"Biologically acceptable" is material that is not known to produce an adverse effect on the tissue or health of an animal upon administration of the material to the animal in a typical amount used in a therapeutic or diagnostic procedure. Example biologically acceptable materials include, materials that are absorbable into the animal such as bone wax or suture material, material that is easily removed from the animal by a physiological process such as excretion, or material that is physiologically inert such as glass.

Turning now to one embodiment, FIG. 1a, shows a needle 2 having a shaft 4 with a proximal portion 8 that has a sharpened point 10 for insertion into tissue. The needle 2 also has a distal end 12 that contains a needle hub 14 connected to the shaft 4 and a needle connector 16 for interconnecting the distal end 12 of the needle with another apparatus. The apparatus to which the distal end of the needle is connected may be any component typically used in a tissue implant application, for example, a template for orienting the needle in a three-dimensional array, a stylet for urging the seeds and spacers into the needle shaft, or a preloading tube. Distal end 12 also has receiving end 18 wherein a load sequence of seeds and spacers are loaded into the shaft 4 and where another inserted apparatus, for example a stylet, may be received. The shaft 4 encloses inner space 22, which receives the load of seeds and spacers and has a diameter sized to accommodate the same. An aperture 20 is provided along a portion of the shaft 20 that exposes a portion of the interior space. The aperture is oriented along a longitudinal axis of the shaft 4, and typically is dimensioned to have a length greater than a width so as to form a slit or slot of sufficient length to expose a plurality of seeds and spacers contained within the interior space 22. An example load sequence of a plurality of seeds 5 and spacers 6 is shown in FIG. 1b where a portion 21 of the aperture 20 positioned toward the proximal end 8 of the shaft 4 exposes a portion of the interior space 22 containing the load sequence of seeds 5 and spacers 6, thereby allowing inspection of the load sequence after it has been received into the shaft 4. The aperture has an opening width 23, that is typically smaller than the width of seeds and spacers 25 to retain the seeds and spacers in the interior space so that they are not lost from the shaft 4 through the aperture.

In a typical use of the aforementioned needle device, after seeds are loaded into the receiving end 18, a stylet is inserted into the receiving end 18 to urge the load sequence of seeds 5 and spacers 6 into position in the shaft so that the load sequence can be detected through the aperture 20. Typically, the opening at the proximal end of the needle (not shown) is plugged with a material that can be absorbed by tissue, for example, bone wax or other biologically acceptable surgical paste or wax. The aperture can alternatively be positioned toward the distal end 12 of the shaft 4 to provide a needle where the proximal end 8 does not have an open portion of the aperture. FIG. 1c illustrates an example embodiment, where the aperture is positioned toward the distal end 12 of shaft 4. In this embodiment, the shaft 4 may include one or more stopping mechanisms, for example, deformable spring elements 27 located at the proximal end of the aperture, for example, on an interior wall 28 of the shaft 4 to retain the seeds 5 and spacers 6 in place under the aperture 20. Alternatively, removable stopping mechanism 26 such as another needle or shaft sized to plug the proximal end of the aperture can be momentarily placed into the aperture to hold the load sequence of seeds 5 and spacers 6, then removed to allow the seeds and spacers to be urged toward the proximal end of the needle 8.

The device of FIG. 1 represents an embodiment wherein the device is a needle 2 in that it provides the proximal end 8 of the shaft 4 with a sharpened point 10 for insertion into tissue and the distal end 12 of the shaft 4 for receiving the load the seeds and spacers formed as an integrated unit. This is an assembly of few parts that is useful in some brachytherapy applications, such as in the treatment of prostate cancer. However, other embodiments include other devices and assemblies that are loaded with a sequence of seeds and spacers. Numerous examples of such brachytherapy devices are known in the art. These include, but are not limited to catheters, as described for example, in Pat. No. 4,763,671 to Goffinet, as well as various designs for more complicated needle devices exemplified by Pat. No. 5,242,373 to Scott et al., U.S. Pat. No. 5,928,130 to Schmidt, U.S. Pat. No. 5,938,583 to Grimm, U.S. Pat. No. 5,860,909 to Mick et al., and U.S. Pat. No. 6,030,333 to Sioshansi et al. In addition, the devices methods and systems described herein are useful with a variety of seed and spacer embodiments, for example, the interlocking seed and spacers described in U.S. Pat. No. 6,010,446 to Grimm, and the absorbable, non-deflecting needle of U.S. Pat. No. 4,815,449 to Horowitz. The disclosure of each of these patents are incorporated herein by reference.

FIG. 2 illustrates an embodiment for a multi-component needle assembly 13 that uses a shaft having an aperture for detecting the load sequence of seeds and spacers. The needle assembly 13 includes a needle member 7, having proximal end 8 with a sharpened point 10 for insertion into tissue, and a distal end 17 containing connectors 19. The needle assembly also includes a sleeve member 9. The shaft 3 of the needle member 7 encloses an interior space having a diameter larger than the outer diameter of sleeve member 9 so that the sleeve member 9 can be received into the interior space of the needle member 7. The sleeve member 9 includes a shaft 4 having an aperture 20 positioned along a portion thereof to expose an inner space 22 for viewing the load sequence of seeds 5 and spacers 6. The shaft 4 of the sleeve member 9 may include one or more stopping mechanisms, for example, deformable spring elements 27 attached to the inner wall 28 to retain the seeds and spacers in a first position so that they do not fall out of the proximal end 29. When the sleeve member 9 is fitted into the needle member 7, the proximal end 29 of the shaft 4 is positioned within the proximal end 8 of the needle member. A stylet member 32 of needle assembly 13 has a diameter sized to fit into the interior space 22 of shaft 4, and is used to urge the load sequence of seeds and spacers through the sleeve member and out of the needle portion by the application of force in the direction 34. The force is applied against a distal seed or spacer 30 and transferred through the sequence of seeds 5 and spacers 6 to deform the spring element 27 allowing the seeds and spacers to pass by the spring element 27 and out of the proximal end 8 of the needle member 7. Alternatively, rather than using a spring element as a stopping mechanism, the proximal end 29 of the shaft may be plugged with bone wax or other biologically acceptable surgical paste or material 31 that can be dislodged from the proximal end 29 of the sleeve member upon application of force.

A shaft containing an aperture for detecting the load of seeds and/or spacers is also useful in catheter devices, for example, as described in U.S. Pat. No. 4,763,671. Catheter devices are typically used in brachytherapy applications that use a higher dose of radioactive seeds for treating larger cancers such as may occur in breast cancer. In these higher dose procedures, the radioactive seeds are typically not permanently implanted and allowed to decay in the tissue. Rather, the patient receives multiple, short duration treatments of higher doses, and the radioactive seeds are removed between treatments. The catheter provides a route for repeated accurate insertion of the load sequence of seeds or spacers. The catheter is usually temporarily surgically anchored to a portion of the body to provide a fixed location so that a portion of the tumor can be accurately reached in multiple treatment sessions.

Figure 3:
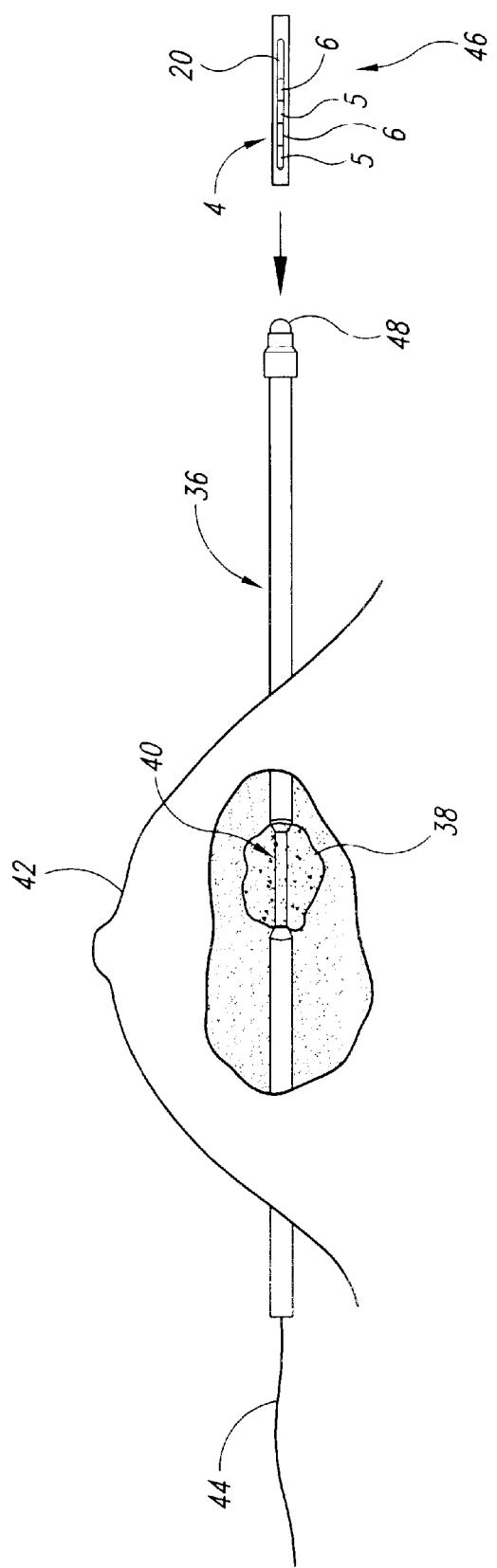
FIG. 3 illustrates another embodiment that includes a catheter loaded with a sequence of seeds and spacers and which contains a shaft having an aperture for inspecting the load sequence prior to insertion into the catheter.

FIG. 3 illustrates an example embodiment where a shaft containing an aperture is used in a catheter application. A catheter member 36 is positioned within breast tissue 42, and has an exposed portion 40 positioned proximate to tumor tissue 38 to provide emitted radiation from a removable sequence of seeds and/or spacers. The seeds and/or spacers are spatially arranged according to a treatment plan to provide an optimal radioactive dose to the tumor 38 with minimal damage to surrounding normal tissue, analogous to treatment of prostate cancer. In some applications, the treatment may include different doses of radioactive seeds in a single load, for example, high dose seeds positioned at the larger interior sections of the tumor, and lower dose seeds positioned at the margins of the tumor.

The load sequence of seeds 5 and/or spacers 6 are arranged in a load shaft 46 that is comprised of a shaft portion 4 and an aperture 20 that exposes the interior space of the shaft for visual inspection of the load sequence of seeds and/or spacers. The load shaft 46 is then attached to an inlet/outlet hub 48 of the catheter 36 and the seeds 5 and/or spacers 6 are pushed or drawn through either end of the catheter 36 using a cannula or wire 44. The radioactive seeds are drawn a predetermined distance into the catheter to place them into position at the exposed portion of the catheter 40 proximate to the tumor 38. In some practices, the radioactive seeds and/or spacers are fitted into a tube or enmeshed in a tissue absorbable material, sized to fit within the interior spaces of the shaft 46 and the entire tube is drawn into the catheter. In other practices, the radioactive seeds or spacers are loosely arranged within the load shaft 46 and drawn into the catheter.

The aperture or slit in the devices of the present invention can be made by a variety of processes known in the art. For example, the shaft 4 can be preformed without an aperture and the aperture can be introduced by cutting the shaft with an appropriate cutting or stamping tool. Typical cutting tools include carbide tipped blades and cutting heads, or lasers. Alternatively, the shaft can be formed in a molding or extrusion process. In a molding process, the shaft is molded in a form that contains an indentation that forms the aperture. In an extrusion process, the shaft is formed by extruding a stream of molten or semi-molten material over a shaping mold, and the aperture is formed by intermittently introducing a stylus into the stream of molten material which is then rapidly cooled into a solid phase leaving the aperture at the points where the stylus was introduced. In a typical practice, the edges surrounding the aperture are polished or beveled to provide smooth edges that will not cut the hands of a technician or inappropriately tear tissue when introduced therein during an implant procedure. The aperture is typically formed in a length suitable to accommodate inspection of a wide number of seeds and spacers used in a diverse number of applications. Typically, the aperture is from about 1 to about 10, typically from about 3 to about 8, and more specifically, from about 5 to about 7 cm in length and from about 0.25 to about 1 mm in width.

The aperture may optionally be enclosed by a transparent or translucent cover so that the interior space 23 of the shaft 4 is visually exposed but not physically exposed. FIG. 4 illustrates a device having shaft 4 and aperture 20, wherein the aperture 20 is covered by a transparent or translucent material 48. Typical examples of transparent or translucent materials include, but are not limited to, glass, polycarbonate, polyethylene, or polypropylene. In one example, the transparent or translucent cover 48 can be provided by a hollow polyethylene tube 50, that has an interior diameter 52, that is greater than the exterior diameter 54, of shaft 4. The hollow polyethylene tube 50 is fit over the exterior of the shaft and positioned over the aperture to provide the transparent cover. In other examples, the shaft may be manufactured with the transparent or translucent material fused to the outer edges of the aperture 55 to provide a smooth outer surface for the shaft 4.

Figure 5A:
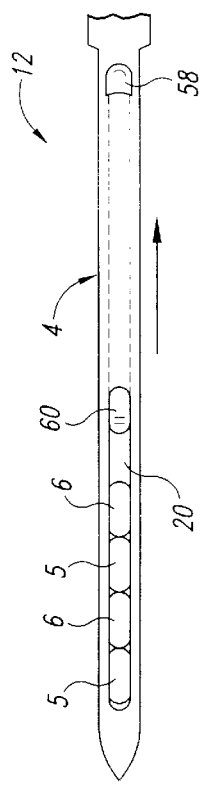
FIG. 5 illustrates embodiments where the aperture is selectably in an open or closed position.
Figure 5B:
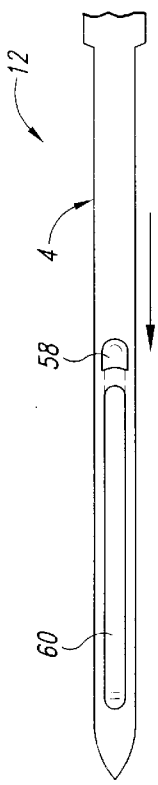
Figure 5C:
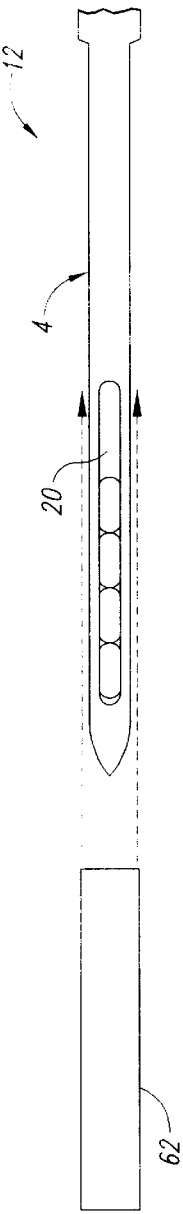
Figure 5D:
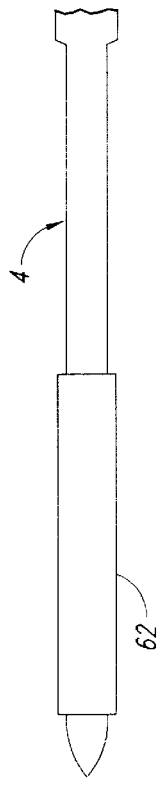

In another optional aspect, the aperture may be selectably placed in an open or closed position. In the open position, a portion of the interior space is exposed through the aperture, allowing detection of the load sequence of seeds and spacers, while in the closed position, the portion of the interior space is not exposed. An example is illustrated in FIG. 5 which shows a shaft having aperture 20 and closure panel 60 that is slidably mounted on shaft 4. In the open position shown in FIG. 5a, the closure panel is pulled back toward the distal portion 12 of the shaft, using grip 58, exposing the interior space of the shaft through aperture 20. In a closed position (5b), the panel is slid forward toward the proximal end 8 of the shaft so as to cover aperture 20. In another embodiment, shown in FIGS. 5c–5d, no closure panel is used, rather the entire shaft 4 is slid into a hollow covering tube 62 made of opaque material. Typically, the opaque material is selected to block radiation emitted from a radioactive seed. When the shaft 4 is slid into the hollow covering tube 62, the aperture is covered as shown in FIG. 5d. When the shaft is slid out of the hollow covering tube, the aperture is open and the seeds and spacers can be detected through the aperture as shown in FIG. 5c.

The device containing the aperture is optionally pre-loaded with a pre-defined sequence of seeds and spacers. In a typical practice, the device is pre-loaded by a supplier according to an individualized treatment plan that lists the sequence of seeds and spacers for each of a plurality of shafts or needles. In another aspect, a plurality of devices is pre-loaded by the supplier according to commonly used treatment plans, and a device having a packing sequence that most clearly matches an individual treatment plan is selected for use. The load sequence of the seeds and spacers is then confirmed by the technician at the time of treatment, merely by inspecting the load sequence of seeds and spacers through the aperture.

There is also provided methods of detecting a load sequence of seeds and spacers that includes the steps of receiving or providing a sequence of seeds and spacers into a shaft, wherein the shaft has an aperture positioned along a portion of the shaft to expose the interior space, and positioning the load sequence of seeds and spacers so that they are detectable through the aperture. In one embodiment, the seeds and spacers are provided pre-loaded into the device by a supplier. In another embodiment, the seeds and spacers are loaded by a technician and confirmed prior to being implanted into tissue.

The foregoing description refers, by example, to devices with apertures that typically are used in brachytherapy applications. However any device used in any application where a sequence of seeds and spacers is to be implanted into tissue can be equipped with an aperture in a shaft portion of the device for viewing the sequence of seeds and spacers after they have been loaded into the shaft. In a typical practice, the aperture is sized to allow easy visual inspection of the load sequence by eye. A typical practice uses a shaft from about a 12 to about a 22 gauge (or larger), and an aperture width of about 0.25 to about 2 mm, and more specifically about 0.9 mm. In an application for treating prostate cancer, the shaft is typically a 17–18 gauge needle with an aperture of about a 0.8–1 mm.

In addition, because the load sequence of seeds and spacers forms a pattern, whenever the color or shape of the seeds and spacers are distinguishable from one another, the pattern can be detected by a machine such as a bar-code reader. Where the load sequence is detected by a machine, the width of the aperture need be only wide enough to receive the detection beam of the machine. Example bar code readers suitable for this use include a variety of hand held scanners available from Symbol Technologies (Bellevue, Wash.). These portable computer-aided scanners include programmable display features to allow a display of the scanned sequence according to user selected criteria. A suitable display would indicate a series of digits as a one or zero in sequence, with the one or the zero corresponding to a seed or spacer.

In a related aspect, the invention provides for colored seeds and/or colored spacers to facilitate optical or visual inspection of the load sequence of seeds or spacers. In this aspect, at least one of the seeds or spacers is colored with a biologically acceptable dye, the color being an identifying color that distinguishes the seeds from the spacers. Typically, the dye is a fluorescent dye. Suitable biologically acceptable dyes include, but are not limited to, inorganic pigments, organic dyes, metallic lakes thereof, chromophores such as anthocyanins, chlorophyll, carotene, or stains such as disulphine blue, methylene blue, toluidine blue, Evan's blue, indocyanine green, D & C Green #6, gentian violet, and iodine. In embodiments where the seed is colored, an anticancer dye may be used to further enhance the therapeutic benefit of the implant. Example anticancer dye substances include a) doxorubicin and its close chemical relative, epirubicin, which are colored red, b) mitomycin-C which is an effective chemotherapeutic agent particularly suitable for localized treatment of bladder cancer and which is violet colored; and c) itoxantrane which is a blue dye and a potent anticancer drug. The concentrations needed for all of the dye substances are in the range of from about 0.001% to about 1%, typically from about 0.01% to about 0.05%, and more specifically from about 0.02% to about 0.03% of the weight of the seed or spacer.

In one embodiment, only the spacers are colored and the seeds are not. In another embodiment only the seeds are colored and the spacers are not. In still another embodiment, both the seeds and spacers are colored differently. In any embodiment, the seeds and/or spacers are optionally colored according to additional criteria to facilitate visual confirmation of a load sequence according to a particular treatment plan. For example, radioactive seeds are available from numerous manufacturers such as Theragenics Corp., (Buford, Ga.) Indigo Inc., (Cincinnati, Ohio), MediPhysics (Arlington Heights, Ill.) or Mentor Corp., (Santa Barbara, Calif.) and available in a variety of isotopes including Iodine-125, Palladium-103, Iridium-192, Radon-222, Strontium-90, and Gold-198. In addition, seeds containing these isotopes come in various doses and the doses are referenced to an assay date that takes into consideration the radioactive half-life of the isotope. Similarly, spacers come from a variety of manufacturers in different sizes and are made from different materials. Any of the aforementioned identifying features of seeds or spacers can serve as criteria for colorcoding. For example, seeds of different isotopes can be assigned to different color groups such as red and green, and the color groups can be further divided into light or dark to distinguish dose amounts. Similarly spacers can be assigned to different color groups by size or material, where the color groups are selected to highlight the differences between the seeds and spacers to make them easily distinguishable by the human eye or by a mechanical scanning device.

Figure 6A:
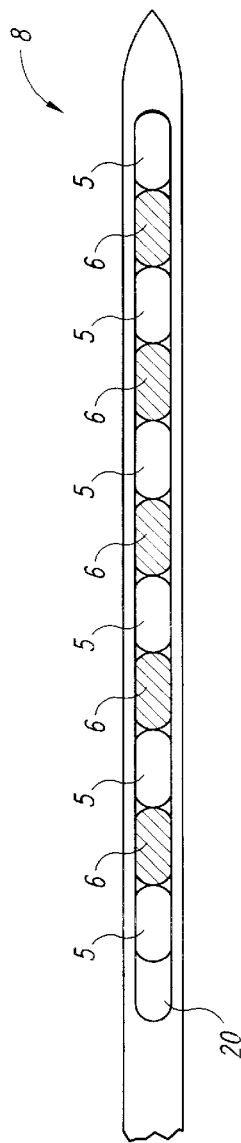
FIG. 6 illustrates colored seeds and/or spacers for use in detecting a sequence thereof.
Figure 6B:
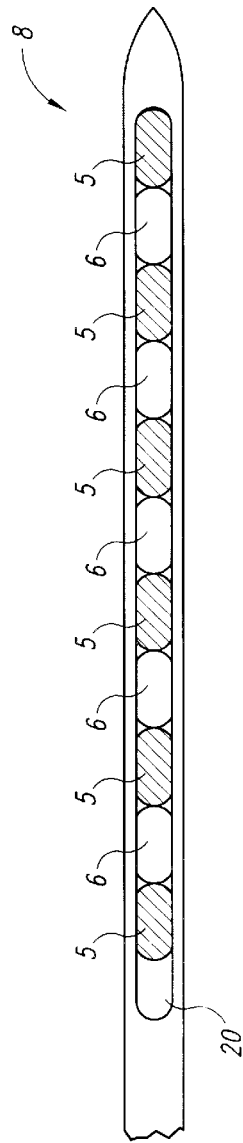
Figure 6C:
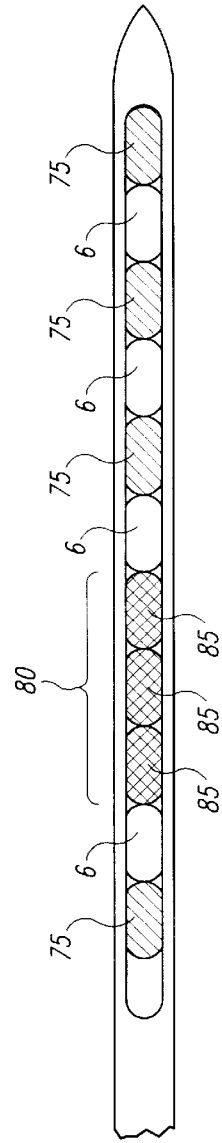

FIG. 6 illustrates these different embodiments using different coloring schemes for a therapeutic load of sequence and spacers. In FIG. 6a, the seeds 5 are not colored and the spacers are colored. FIG. 6b shows an identical load sequence where the seeds 5 are colored and the spacers 6 are not colored. In FIG. 6c, the spacers 6 are not colored and the seeds 75 and 85 are colored with different colorants to identify different doses of radioactivity, with higher doses 85 being positioned in a central position that will correspond to a larger section of the tumor when implanted, and lower doses 75 being distributed to correspond to smaller sections of the tumor. In each of these embodiments, the seeds and spacers are visible through the aperture 20. The technician can refer to a visual or textual instruction or map that corresponds to the treatment plan for each needle, and can confirm the load sequence by comparing the actual sequence to the instructions for the planned sequence.

The use of colored seeds and/or spacers provides a system and method for detecting the load sequence of seeds or spacers by identifying the colors of the loaded material. The system may optionally include instructions such as a checklist, reference list, and/or map that references the colored seeds or spacers according to various criteria and/or a treatment plan.

For example, the system may include a list of needles labeled 1-n, where n is the number of needles, and corresponding instructions that list a sequence of colors representing a particular isotope, loaded into each needle according to a treatment plan. As a more specific example, the treatment plan might call for two needles loaded with a different sequence of Iridium-103 seeds and spacers. The instructions would recite, for example, that Iridium-103 is red;

spacers are white, needle 1 is loaded: red, white, white, red; needle 2 is loaded: red, red, red, white. In a method of use, the seeds and spacers are first received or arranged in a load sequence, and the technician seeking to confirm the load sequence need only verify the color sequence without reference to whether it is a seed or spacer. This system and method is useful in any application where a sequence of seeds and spacers is to be implanted into tissue. In one practice, the system is used in combination with any of the aforementioned devices containing an aperture in a shaft to facilitate detection by observing the sequence of seeds and spacers through the aperture.

The foregoing description is intended to illustrate example embodiments of the devices, systems and methods of the present invention. One of ordinary skill in the art can use this disclosure to practice the invention in numerous other embodiments without departing from the scope of the invention. The invention is therefore, not limited by the foregoing description except as by the following claims

What is claimed is:

1. A device for implanting seeds and spacers into tissue comprising, a shaft enclosing an interior space for receiving a load sequence of seeds and/or spacers, the shaft containing an aperture positioned along a portion of the shaft toward a proximal end that is inserted into to the tissue, the aperture exposing a portion of the interior space sufficient to detect the load sequence of seeds and spacers after said load has been received into the shaft, the aperture being selectably in an open position where a portion of the interior space is exposed allowing detection of the load sequence of seeds and spacers, or in a closed position where the portion of the interior space is not exposed.

2. The device of claim 1 wherein the seeds are radioactive seeds used in a brachytherapy procedure.

3. The device of claim 2 wherein the brachytherapy procedure is for treatment of prostate cancer.

4. The device of claim 1 wherein the aperture is a slit along a longitudinal axis of the shaft.

5. The device of claim 1 wherein the shaft is a needle having the proximal end for insertion into tissue and a distal end for receiving a stylet for urging the load sequence of seeds and spacers into the tissue.

6. The device of claim 1 wherein the shaft is a sleeve member that is received into a needle member, wherein the needle member also has a proximal end for insertion into tissue and has a distal end for receiving the sleeve member.

7. The device of claim 1 wherein the shaft is received into a catheter member, wherein the catheter member provides a route for inserting the load of spacers and seeds into tissue.

8. The device of claim 1 wherein the aperture is also positioned a toward a distal end of the shaft, wherein the distal end receives a stylet for urging the load sequence of seeds and spacers into the tissue.

9. The device of claim 1 further including a stopping mechanism that holds the load sequence of seeds and spacers in a first position where the load sequence is visible through the aperture.

10. The device of claim 1 wherein the aperture is sized to allow visual detection of load sequence of seeds and spacers.

11. The device of claim 1 wherein the load sequence of the seeds and spacers is detected by an optical scanning device.

12. The device of claim 1 wherein the aperture extends for a distance of about 5–7 cm along a longitudinal axis of the shaft.

13. The device of claim 1 wherein the aperture is covered by a transparent or translucent material.

14. The device of claim 1 that is pre-loaded with a sequence of seeds and spacers, wherein the sequence of seeds and spacers is selected according to an individual or common treatment plan.

15. The device of claim 1 wherein the shaft is used in a brachytherapy treatment of prostate cancer.

16. A seed for implanting into tissue in a load sequence with a spacer, wherein the seed is colored with a biologically acceptable dye to identify the seed.

17. The seed of claim 16 wherein the seed is radioactive.

18. The radioactive seed of claim 16 wherein the seed is colored to identify the seed by criteria selected from the group consisting of isotope, dose, assay date or manufacturer.

19. The seed of claim 16 wherein the seed is colored with a fluorescent dye.

20. The seed of claim 16 wherein the seed is colored with a dye selected to distinguish the seed from a color of a spacer.

21. The seed of claim 16 wherein the seed is colored with a dye that has anti-tumor properties.

22. A spacer for implanting into tissue in a load sequence with a radioactive seed, wherein the spacer is colored with a biologically acceptable dye to identify the spacer.

23. The spacer of claim 22 wherein the spacer colored to identify the spacer by criteria selected from the group consisting of size, material or manufacturer.

24. The spacer of claim 22 wherein the spacer is colored with a fluorescent dye.

25. The spacer of claim 22 wherein the spacer is colored with a dye selected to distinguish the spacer from a color of a radioactive seed.

26. A system for detecting a load sequence of seeds and spacers in a loading shaft, comprising seeds and spacers, wherein at least one of the seeds or spacers is colored with a biologically acceptable dye to provide an identifying color that distinguishes the seeds from the spacers.

27. The system of claim 26 wherein the spacers are colored and the seeds are not colored.

28. The system of claim 26 wherein the seeds are colored and the spacers are not colored.

29. The system of claim 26 wherein at least one of the seeds or spacers is colored with a fluorescent dye.

30. The system of claim 22 wherein the seeds are colored with a first color and the spacers are colored with a second color.

31. The system of claim 22 wherein the seeds are colored to identify the seeds by criteria selected from the group consisting of isotope, dose, assay date or manufacturer.

32. The system of claim 22 wherein the spacers are colored to identify the seeds by criteria selected from the group consisting of size, material or manufacturer.

33. The system of claim 26 further including a brachytherapy device loaded with the colored seeds or spacers.

34. The system of claim 33 wherein the device is preloaded with the colored seeds or spacers according to an individual or common treatment plan.

35. The system of claim 34 further including instructions, a map, or a list that corresponds to the sequence of colored seeds or spacers.

36. The system of claim 26 used in a brachytherapy treatment of prostate cancer.

37. A method for detecting a load sequence of seeds and spacers in a brachytherapy device comprising, receiving a load sequence of seeds and spacers into a shaft enclosing an interior space that receives the load sequence of seeds and spacers, wherein the shaft contains an aperture positioned along a portion of the shaft toward a proximal end that is inserted into to the tissue, the aperture exposing a portion of the interior space, the aperture being selectably in an open position where a portion of the interior space is exposed allowing detection of the load sequence of seeds and spacers, or in a closed position where the portion of the interior space is not exposed; and positioning the load sequence of seeds and spacers in the shaft so that the load sequence of seeds and spacers is detected through the aperture.

38. The method of claim 37 wherein the aperture is a slit along a longitudinal axis of the shaft.

39. The method of claim 37 wherein the shaft is a needle having the proximal end for insertion into tissue and has a distal end for receiving a stylet for urging the load sequence of seeds and spacers into the tissue.

40. The method of claim 37 wherein the shaft is a sleeve member that is received into a needle member, wherein the needle member has the proximal end for insertion into tissue and has a distal end for receiving the sleeve member.

41. The method of claim 37 wherein the shaft is received into a catheter member, wherein the catheter member provides a route for inserting the load of spacers and seeds into tissue.

42. The method of claim 37 wherein the shaft is preloaded with the sequence of seeds and spacers according to an individual or common treatment plan.

43. The method of claim 37 used in a brachytherapy treatment of prostate cancer.

44. A method of detecting a load sequence of seeds and spacers in a brachytherapy device comprising, receiving a load sequence of seeds and spacers into a device, wherein at least one of the seeds or spacers is colored with a biologically acceptable dye to provide an identifying color that distinguishes the seeds from the spacers; and detecting the load sequence by detecting the position of the colored seeds or spacers.

45. The method of claim 44 wherein the spacers are colored and the seeds are not colored.

46. The method of claim 44 wherein the seeds are colored and the spacers are not colored.

47. The method of claim 44 wherein at least one of the seeds or spacers is colored with a fluorescent dye.

48. The method of claim 44 wherein the seeds are colored with a first color and the spacers are colored with a second color.

49. The method of claim 44 wherein the seeds are colored to identify the seeds by criteria selected from the group consisting of isotope, dose, or manufacturer.

50. The method of claim 44 wherein the spacers are colored to identify the seeds by criteria selected from the group consisting of size, material or manufacturer.0000.

51. The method of claim 44 further including loading the seeds and spacers into a shaft enclosing an interior space for receiving the load sequence of seeds and spacers, wherein the shaft contains an aperture positioned along a portion of the shaft that exposes a portion of the interior space, and positioning the load sequence of seeds and spacers in the shaft so that the load sequence of seeds and spacers in the interior space is detectable through the aperture.

52. The method of claim 51 wherein the aperture is a slit along a longitudinal axis of the shaft.

53. The method of claim 51 herein the shaft is needle having a proximal end for insertion into tissue and has a distal end for receiving a stylet for urging the load sequence of seeds and spacers into the tissue.

54. The method of claim 51 wherein the shaft is a sleeve member that is received into a needle member, wherein the needle member has a proximal end for insertion into tissue and has a distal end for receiving the sleeve member.

55. The method of claim 51 wherein the shaft is received into a catheter member, wherein the catheter member provides a route for inserting the load of spacers and seeds into tissue.

56. The method of claim 44 used in a brachytherapy treatment of prostate cancer.

57. The method of claim 51 used in a brachytherapy treatment of prostate cancer.

* * * * *